US012311095B2

(12) United States Patent
Biller et al.

(10) Patent No.: US 12,311,095 B2
(45) Date of Patent: May 27, 2025

(54) MULTI-LUMEN CANNULAE

(71) Applicant: EDWARDS LIFESCIENCES CORPORATION, Irvine, CA (US)

(72) Inventors: William T. Biller, Tustin, CA (US); Manouchehr A. Miraki, Laguna Hills, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/522,232

(22) Filed: Nov. 29, 2023

(65) Prior Publication Data
US 2024/0091426 A1   Mar. 21, 2024

Related U.S. Application Data

(63) Continuation of application No. 16/820,614, filed on Mar. 16, 2020, now Pat. No. 11,857,744, which is a
(Continued)

(51) Int. Cl.
*A61M 1/36* (2006.01)
*A61M 1/00* (2006.01)
(Continued)

(52) U.S. Cl.
CPC ............ *A61M 1/3666* (2013.01); *A61M 1/84* (2021.05); *A61M 1/85* (2021.05); *A61M 25/003* (2013.01);
(Continued)

(58) Field of Classification Search
CPC ........ A61M 1/14; A61M 1/1698; A61M 1/32; A61M 1/36; A61M 1/3621; A61M 1/3666;
(Continued)

(56) References Cited

U.S. PATENT DOCUMENTS 528,759 A    11/1894  Bernhardt
3,143,742 A   8/1964  Cromie
(Continued)

FOREIGN PATENT DOCUMENTS

DE    29911694 U1   8/1999
EP    0125393 A1   11/1984
(Continued)

OTHER PUBLICATIONS

"Freestyle Aortic Root Bioprosthesis", Medtronic Bioprosthesis for Replacement of Malfunctioning Native or Prosthetic Aortic Valve, 4 pages, [online], [retrieved on Oct. 19, 2011]. Retrieved from the internet <URL:http://www.medtronic.com/for-healthcare-professionals/products-therapies/cardiovascula . . . .
(Continued)

*Primary Examiner* — Shefali D Patel
(74) *Attorney, Agent, or Firm* — Klarquist Sparkman, LLP

(57) ABSTRACT

The present disclosure concerns embodiments of multi-lumen cannulae that can be used in various different medical procedures. The multi-lumen cannulae can comprise an elongated body comprising multiple different ports that connect to various different sidewall lumens contained within the elongated body. The multi-lumen cannulae can also comprise a central lumen that extends through the entire elongated body and can be fluidly connected to the various different sidewall lumens. The multi-lumen cannulae can further comprise two balloons on an exterior of the elongated body, which can be used to isolate a right atrium of a patient's heart.

15 Claims, 11 Drawing Sheets

Related U.S. Application Data continuation of application No. 15/501,801, filed as application No. PCT/US2015/044003 on Aug. 6, 2015, now abandoned.

(60) Provisional application No. 62/033,987, filed on Aug. 6, 2014.

(51) Int. Cl.
- *A61M 25/00* (2006.01)
- *A61M 25/10* (2013.01)
- *A61M 1/16* (2006.01)

(52) U.S. Cl.
CPC .......... *A61M 25/007* (2013.01); *A61M 25/10* (2013.01); *A61M 25/1011* (2013.01); *A61M 1/1698* (2013.01); *A61M 25/0032* (2013.01); *A61M 2025/0036* (2013.01); *A61M 2025/004* (2013.01); *A61M 2025/105* (2013.01); *A61M 2025/1052* (2013.01); *A61M 2025/1097* (2013.01); *A61M 2210/125* (2013.01)

(58) Field of Classification Search
CPC ........ A61M 1/3667; A61M 1/84; A61M 1/85; A61M 1/87; A61M 2025/0031; A61M 2025/0036; A61M 2025/0037; A61M 2025/004; A61M 2025/105; A61M 2025/1052; A61M 2025/1061; A61M 2025/1095; A61M 2025/1097; A61M 2202/0413; A61M 2210/12; A61M 2210/125; A61M 25/0023; A61M 25/0026; A61M 25/0028; A61M 25/0029; A61M 25/003; A61M 25/0032; A61M 25/007; A61M 25/0071; A61M 25/10; A61M 25/1011

See application file for complete search history.

(56) References Cited

U.S. PATENT DOCUMENTS

| | | |
|---|---|---|
| 3,164,009 A | 1/1965 | Schaschl |
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,016,867 A | 4/1977 | King et al. |
| 4,035,849 A | 7/1977 | Angell et al. |
| 4,056,854 A | 11/1977 | Boretos et al. |
| 4,062,911 A | 12/1977 | Pepping |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,185,638 A | 1/1980 | Bruner |
| 4,211,241 A | 7/1980 | Kaster et al. |
| 4,217,665 A | 8/1980 | Bex et al. |
| 4,218,782 A | 8/1980 | Rygg |
| 4,252,131 A | 2/1981 | Hon et al. |
| 4,259,753 A | 4/1981 | Liotta et al. |
| 4,340,091 A | 7/1982 | Skelton et al. |
| 4,343,048 A | 8/1982 | Ross et al. |
| 4,362,167 A | 12/1982 | Nicolai et al. |
| 4,364,126 A | 12/1982 | Rosen et al. |
| 4,372,743 A | 2/1983 | Lane |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,585,453 A | 4/1986 | Martin et al. |
| 4,602,911 A | 7/1986 | Ahmadi et al. |
| 4,605,407 A | 8/1986 | Black et al. |
| 4,626,255 A | 12/1986 | Reichart et al. |
| 4,629,459 A | 12/1986 | Ionescu et al. |
| 4,643,194 A | 2/1987 | Fogarty |
| 4,679,556 A | 7/1987 | Lubock et al. |
| 4,680,031 A | 7/1987 | Alonso |
| 4,685,474 A | 8/1987 | Kurz et al. |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,898,155 A | 2/1990 | Ovil et al. |
| 4,914,097 A | 4/1990 | Oda et al. |
| 4,940,459 A | 7/1990 | Noce |
| 4,960,424 A | 10/1990 | Grooters |
| 4,993,428 A | 2/1991 | Arms |
| 5,010,892 A | 4/1991 | Colvin et al. |
| 5,011,481 A | 4/1991 | Myers et al. |
| 5,032,128 A | 7/1991 | Alonso |
| 5,037,434 A | 8/1991 | Lane |
| 5,042,161 A | 8/1991 | Hodge |
| 5,053,008 A | 10/1991 | Bajaj |
| 5,089,015 A | 2/1992 | Ross |
| 5,147,391 A | 9/1992 | Lane |
| 5,163,955 A | 11/1992 | Love et al. |
| 5,171,248 A | 12/1992 | Ellis |
| 5,197,979 A | 3/1993 | Quintero et al. |
| 5,236,450 A | 8/1993 | Scott |
| 5,258,023 A | 11/1993 | Reger |
| 5,290,300 A | 3/1994 | Cosgrove et al. |
| 5,312,344 A | 5/1994 | Grinfeld et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,460,610 A * | 10/1995 | Don Michael .... A61M 25/0133 604/101.03 |
| 5,469,868 A | 11/1995 | Reger |
| 5,471,756 A | 12/1995 | Bolanos et al. |
| 5,476,510 A | 12/1995 | Eberhardt et al. |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,496,346 A | 3/1996 | Horzewski et al. |
| 5,500,016 A | 3/1996 | Fisher |
| 5,531,785 A | 7/1996 | Love et al. |
| 5,533,515 A | 7/1996 | Coller et al. |
| 5,545,214 A | 8/1996 | Stevens |
| 5,549,665 A | 8/1996 | Vesely et al. |
| 5,562,729 A | 10/1996 | Purdy et al. |

(56) References Cited

U.S. PATENT DOCUMENTS

| | | |
|---|---|---|
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,584,878 A | 12/1996 | Love et al. |
| 5,618,307 A | 4/1997 | Donlon et al. |
| 5,626,607 A | 5/1997 | Malecki et al. |
| 5,628,789 A | 5/1997 | Vanney et al. |
| 5,653,749 A | 8/1997 | Love et al. |
| 5,662,705 A | 9/1997 | Love et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,716,417 A | 2/1998 | Girard et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,096 A | 9/1998 | Lam et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,843,177 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,885,228 A | 3/1999 | Rosenman et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,001,126 A | 12/1999 | Nguyen-Thien-Nhon |
| 6,010,511 A | 1/2000 | Murphy |
| 6,010,531 A | 1/2000 | Donlon et al. |
| 6,019,739 A | 2/2000 | Rhee et al. |
| 6,042,554 A | 3/2000 | Rosenman et al. |
| 6,042,607 A | 3/2000 | Williamson, IV et al. |
| 6,045,576 A | 4/2000 | Starr et al. |
| 6,050,973 A | 4/2000 | Duffy |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,099,506 A | 8/2000 | Macoviak et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,136,017 A | 10/2000 | Craver et al. |
| 6,166,184 A | 12/2000 | Hendriks et al. |
| 6,197,014 B1 | 3/2001 | Samson et al. |
| 6,210,338 B1 | 4/2001 | Afremov et al. |
| 6,214,054 B1 | 4/2001 | Cunanan et al. |
| 6,264,611 B1 | 7/2001 | Ishikawa et al. |
| 6,319,281 B1 | 11/2001 | Patel |
| 6,322,526 B1 | 11/2001 | Rosenman et al. |
| 6,350,281 B1 | 2/2002 | Rhee |
| 6,350,282 B1 | 2/2002 | Eberhardt |
| 6,491,624 B1 | 12/2002 | Lotfi |
| 6,533,770 B1 | 3/2003 | Lepulu et al. |
| 6,582,419 B1 | 6/2003 | Schoon et al. |
| 6,598,307 B2 | 7/2003 | Love et al. |
| 6,626,872 B1 | 9/2003 | Navia et al. |
| 6,669,674 B1 | 12/2003 | Macoviak et al. |
| 6,726,651 B1 * | 4/2004 | Robinson ......... A61B 17/12136 604/4.01 |
| 6,773,457 B2 | 8/2004 | Ivancev et al. |
| 6,802,860 B2 | 10/2004 | Cosgrove et al. |
| 6,846,324 B2 | 1/2005 | Stobie |
| 6,942,694 B2 | 9/2005 | Liddicoat et al. |
| 7,007,396 B2 | 3/2006 | Rudko et al. |
| 7,018,404 B2 | 3/2006 | Holmberg et al. |
| 7,037,333 B2 | 5/2006 | Myers et al. |
| 7,258,698 B2 | 8/2007 | Lemmon |
| 7,270,142 B2 | 9/2007 | Acosta |
| 7,351,197 B2 | 4/2008 | Montpetit et al. |
| 7,637,943 B2 | 12/2009 | Lemmon |
| 7,713,216 B2 | 5/2010 | Dubey et al. |
| 7,842,084 B2 | 11/2010 | Bicer |
| 7,998,151 B2 | 8/2011 | St. Goar et al. |
| 8,057,396 B2 | 11/2011 | Forster et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,449,625 B2 | 5/2013 | Campbell et al. |
| 8,475,521 B2 | 7/2013 | Suri et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0055773 A1 | 5/2002 | Campbell et al. |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0004452 A1 | 1/2003 | Lenker |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0176830 A1 | 9/2003 | Scheule |
| 2003/0191416 A1 | 10/2003 | Rosenman et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0148017 A1 | 7/2004 | Stobie |
| 2004/0167573 A1 | 8/2004 | Williamson et al. |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0215235 A1 | 10/2004 | Jackson et al. |
| 2004/0225355 A1 | 11/2004 | Stevens |

(56) References Cited

U.S. PATENT DOCUMENTS

| | | |
|---|---|---|
| 2004/0236411 A1 | 11/2004 | Sarac et al. |
| 2004/0237321 A1 | 12/2004 | Rudko et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222532 A1 | 10/2005 | Bertolero et al. |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004398 A1 | 1/2006 | Binder et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0144441 A1 | 7/2006 | Acosta |
| 2006/0149360 A1 | 7/2006 | Schwammenthal et al. |
| 2006/0154230 A1 | 7/2006 | Cunanan et al. |
| 2006/0155321 A1 | 7/2006 | Bressler et al. |
| 2006/0161249 A1 | 7/2006 | Realyvasquez et al. |
| 2006/0167543 A1 | 7/2006 | Bailey et al. |
| 2006/0195134 A1 | 8/2006 | Crittenden |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241743 A1 | 10/2006 | Bergin et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271000 A1 | 11/2006 | Ranalletta et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287718 A1 | 12/2006 | Bicer |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2007/0299513 A1 | 12/2007 | Ryan et al. |
| 2008/0009746 A1 | 1/2008 | Forster et al. |
| 2008/0021546 A1 | 1/2008 | Patz et al. |
| 2008/0033543 A1 | 2/2008 | Gurskis et al. |
| 2008/0033544 A1 | 2/2008 | Lemmon |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0208331 A1 | 8/2008 | McCarthy et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0069890 A1 | 3/2009 | Suri et al. |
| 2009/0093877 A1 | 4/2009 | Keidar et al. |
| 2009/0132036 A1 | 5/2009 | Navia |
| 2009/0182419 A1 | 7/2009 | Bolling |
| 2009/0192599 A1 | 7/2009 | Lane et al. |
| 2009/0192600 A1 | 7/2009 | Ryan |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0234291 A1 | 9/2009 | Saunders et al. |
| 2010/0152844 A1 | 6/2010 | Couetil |
| 2010/0161036 A1 | 6/2010 | Pintor et al. |
| 2010/0241068 A1 | 9/2010 | Chen |
| 2010/0249661 A1 | 9/2010 | Righini et al. |

(56) References Cited

U.S. PATENT DOCUMENTS

| | | |
|---|---|---|
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0040372 A1 | 2/2011 | Hansen et al. |
| 2011/0147251 A1 | 6/2011 | Hodshon et al. |
| 2011/0152741 A1 | 6/2011 | Banchieri et al. |
| 2012/0016408 A1 | 1/2012 | Barbut et al. |
| 2012/0065729 A1 | 3/2012 | Pintor et al. |
| 2012/0071968 A1 | 3/2012 | Li et al. |
| 2012/0141656 A1 | 6/2012 | Orr et al. |
| 2012/0150288 A1 | 6/2012 | Hodshon et al. |
| 2012/0259273 A1 | 10/2012 | Moshinsky et al. |
| 2012/0302953 A1 | 11/2012 | Don Michael |
| 2013/0053949 A1 | 2/2013 | Pintor et al. |
| 2013/0116777 A1 | 5/2013 | Pintor et al. |
| 2013/0150954 A1 | 6/2013 | Conklin |
| 2014/0058194 A1 | 2/2014 | Soletti et al. |
| 2014/0079758 A1 | 3/2014 | Hall et al. |

FOREIGN PATENT DOCUMENTS

| | | |
|---|---|---|
| EP | 0143246 A2 | 6/1985 |
| EP | 0619745 A1 | 10/1994 |
| EP | 2080474 A1 | 7/2009 |
| FR | 2681775 A1 | 4/1993 |
| GB | 2083362 A | 3/1982 |
| GB | 2137499 A | 10/1984 |
| SU | 1116573 A1 | 7/1985 |
| SU | 1697790 A1 | 12/1991 |
| WO | 8102098 A1 | 8/1981 |
| WO | 8705489 A1 | 9/1987 |
| WO | 9213502 A1 | 8/1992 |
| WO | 9418909 A2 | 9/1994 |
| WO | 9516410 A1 | 6/1995 |
| WO | 9640006 A1 | 12/1996 |
| WO | 9725003 A1 | 7/1997 |
| WO | 9741801 A1 | 11/1997 |
| WO | 9742871 A1 | 11/1997 |
| WO | 9964099 A1 | 12/1999 |
| WO | 0150985 A1 | 7/2001 |
| WO | 2006093273 A1 | 9/2006 |
| WO | 2007146261 A2 | 12/2007 |
| WO | 2010090720 A1 | 8/2010 |
| WO | 2010111621 A1 | 9/2010 |
| WO | 2011097355 A2 | 8/2011 |
| WO | 2011106354 A1 | 9/2011 |

OTHER PUBLICATIONS

A. Sidiropoulos, et al., Stentless Porcine Bioprostheses for all Types of Aortic Root pathology, European Journal of Cardio-Thoracic Surgery, 1997:11:917-921.

Int'l. Search Report for PCT/US2015/036005, Mailed Sep. 21, 2015.

Int'l. Search Report for PCT/US2015/044003, Mailed Nov. 11, 2015.

Krakow, "3F Therapeutics, Inc. Announces the First Clinical Implantation of the 3F Enable Aortic Heart ValveTM, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 12.

Neal D. Kon, MD, et al., Comparison of Implantation Techniques Using Freestyle Stentles Porcine Aortic Valve, The Society of Thoracic Surgeons 1995, pp. 857-862.

Stephen Westaby, et al., Aortic Valve Replacement With the Freestyle Stentless Xenograft, The Society of Thoracic Surgeons 1995, pp. S422-S427.

Stephen Westaby, et al., Time-Related Hemodynamic Changes After Aortic Replacement With the Freestyle Stentless Xenograft, The Society of Thoracic Surgeons 1995, pp. 857-862.

Techniques for 3D Quantitative Echocardiography, University of Washington Cardiovascular Research & Training Center Cardiac Imaging Research Lab, pp. 1-5, Oct. 2003.

* cited by examiner

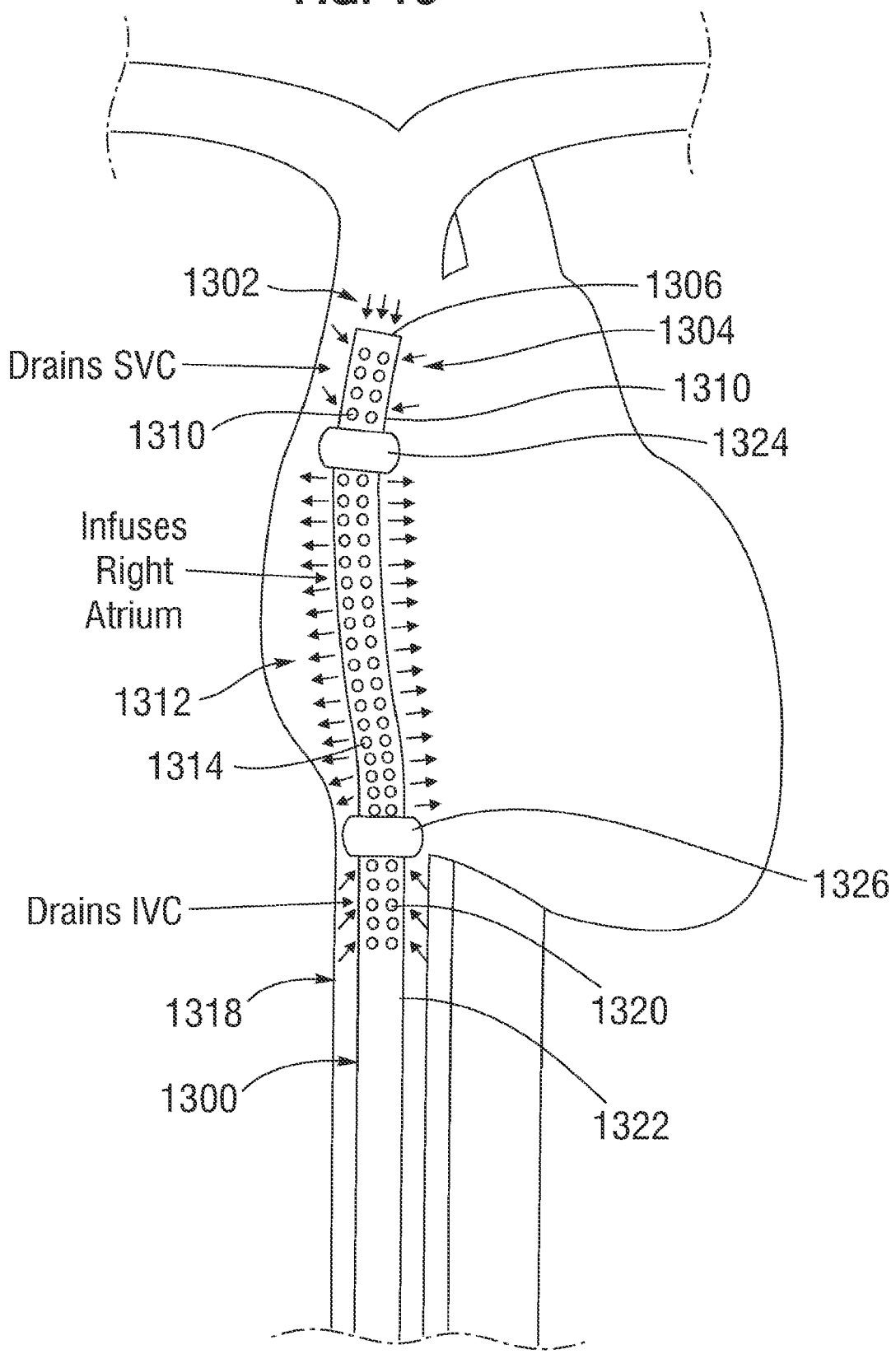

MULTI-LUMEN CANNULAE

CROSS REFERENCE TO RELATED APPLICATIONS

This application is a continuation of U.S. patent application Ser. No. 16/820,614, filed on Mar. 16, 2020, which is a continuation of U.S. patent application Ser. No. 15/501,801, filed on Feb. 3, 2017, which is a U.S. National Stage of International Application No. PCT/US2015/044003, filed Aug. 6, 2015, which claims the benefit of U.S. patent application Ser. No. 62/033,987, filed Aug. 6, 2014, the entire disclosures all of which are incorporated by reference for all purposes.

FIELD

The present disclosure pertains to embodiments of multi-lumen cannulae that can be used to facilitate heart repair and/or other related procedures.

BACKGROUND

Surgically placed cannulae are frequently used in surgical procedures to draw or push blood into patient vessels. In some cases, multiple cannulae must be used during procedures. Current cannulae known in the art are typically made from a single lumen tube with multiple holes at the distal section. Such cannulae, however, cannot perform multiple functions and thus multiple cannulae are required to achieve such functions. As can be appreciated, using multiple cannulae adds complexity to the procedure, which can reduce efficiency and cause lengthy procedures and thereby cause potential patient complications and/or result in lengthy recovery times. Accordingly, a need exists in the art for a single cannula that is capable of performing multiple different functions during a procedure.

SUMMARY

The present disclosure concerns embodiments of multi-lumen cannulae that can be used to facilitate multiple different procedures during an operation, such as a heart operation, within a patient's vasculature. The disclosed multi-lumen cannulae comprise an elongated body having a distal end portion for placement in a biological lumen of a patient and a proximal end portion for placement outside the patient. The multi-lumen cannulae also may have a first balloon and a second balloon connected to an exterior surface of the elongated body in the distal end portion. The first balloon and the second balloon can be configured to fluidly isolate, between the first and second balloons, a portion of the biological lumen of the patient when inflated. The multi-lumen cannulae also comprise a central lumen extending through the elongated body from the distal end portion to the proximal end portion, distal fluid ports and proximal fluid ports in the distal end portion of the elongated body that are fluidly coupled to the central lumen for conducting fluid between the biological lumen of the patient and the central lumen. The multi-lumen cannulae can also comprise at least one balloon sidewall lumen arranged parallel to the central lumen and located within an outer perimeter of the elongated body, and at least one balloon port. The at least one inflation and deflation port can fluidly couple the balloon sidewall lumen to the first balloon, the second balloon, or both, for inflation and deflation of the balloons. The multi-lumen cannulae also can comprise at least one conduction sidewall lumen and at least one intermediate fluid port located in an intermediate region of the distal end portion of the elongated body.

An exemplary embodiment of a multi-lumen cannula can comprise a first balloon sidewall lumen that is coupled to a first inflation and deflation port and a second balloon sidewall lumen that is coupled to a second inflation and deflation port. The multi-lumen cannula also can comprise two conduction sidewall lumens that are fluidly coupled to intermediate fluid ports. In some embodiments, the multi-lumen cannula also can comprise at least one conduction sidewall lumen that is fluidly coupled to at least one distal fluid port, a proximal fluid port, or a combination thereof. Distal fluid ports can be located in the distal region of the distal end portion of the elongated body and proximal fluid ports can be located in the proximal region of the distal end portion of the elongated body.

An exemplary method of using a multi-lumen cannula such as those disclosed herein comprises introducing a multi-lumen cannula into the vena cava of a patient and inflating a first balloon of the cannula within the inferior vena cava and a second balloon of the cannula within the superior vena cava to fluidly isolate the right atrium of the patient from the inferior vena cava or superior vena cava. The method can further comprise draining blood from the patent's inferior vena cava and superior vena cava through at least one distal fluid port in the cannula located distal to the first and second balloons and at least one proximal fluid port in the cannula located proximal to the first and second balloons, and conducting a fluid to or from the right atrium through at least one intermediate fluid port in the cannula located between the first balloon and the second balloon.

An exemplary embodiment of the method can involve introducing the multi-lumen cannula into the patient's vena cava from an inferior access point such that the first balloon is positioned proximal to the second balloon, wherein the inferior access point is in the femoral vein. In another embodiment, the multi-lumen cannula can be introduced into the patient's vena cava from a superior access point such that the first balloon is positioned proximal to the second balloon, wherein the superior access point is in internal jugular vein. The method also may comprise using the distal fluid ports, proximal fluid ports, and intermediate fluid ports to drain blood to a common blood reservoir. In some embodiments, the intermediate ports can drain blood to a first destination and the proximal fluid ports and the distal fluid ports can drain blood to a second destination segregated from the first destination. In exemplary embodiments, the intermediate ports can drain blood to a cell saver for hemoconcentration and the proximal fluid ports and distal fluid ports can drain blood to a cardiotomy reservoir for recirculation.

The foregoing and other objects, features, and advantages of the disclosed technology will become more apparent from the following detailed description, which proceeds with reference to the accompanying figures.

BRIEF DESCRIPTION OF THE DRAWINGS

FIG. 16 shows an exemplary use of a multi-lumen cannula wherein the balloons are inflated, the ports in the distal region and proximal region of the cannula are used to drain blood from the SVC and the IVC, and ports in the intermediate region are used to infuse blood into the right atrium independent of the SVC and IVC.

DETAILED DESCRIPTION

The present disclosure concerns embodiments of multi-lumen cannulae that comprise multiple lumens capable of facilitating a variety of different procedures that may be performed during a heart valve operation and/or other medical procedure. The disclosed multi-lumen cannulae can be used to conduct fluid into or out of vessels during minimally invasive surgery or open heart surgeries. Because the multi-lumen cannulae disclosed herein can comprise multiple lumens within a single cannula body, additional separate cannulae may not be necessary. The disclosed multi-lumen cannulae can therefore provide more efficient means for providing alternative blood flow routes during surgery as multiple different cannulae may not need to be introduced and/or removed from the patient, which can reduce physical stress to the patient and can increase the speed of application of the cannulae.

The disclosed multi-lumen cannulae can also be used to control and/or localize cardioplegia solution delivery to particular sections of the heart, such as the right atrium, thereby preventing mixing in undesired regions of the patients' circulatory system. For example, in some embodiments, blood from the inferior vena cava (referred to herein as "IVC") and the superior vena cava (referred to herein as "SVC") can be isolated from the cardioplegia solution as it is delivered to the patient's heart. The disclosed multi-lumen cannulae also can be kink-resistant, and may not require braided tubing or structure-reinforcing materials for operation.

The examples provided below describe various features of the disclosed multi-lumen cannulae as well as configurations of various portions of the cannulae that can facilitate their use in medical procedures, such as heart valve repairs (e.g., tricuspid valve procedures, mitral valve repairs, or aortic valve repairs), coronary artery bypass grafts, or extracorporeal membrane oxygenation (ECMO) (e.g., veno-arterial ECMO or veno-venous ECMO). Embodiments of the cannulae can be used for blood drainage, blood delivery, and/or cardioplegia solution delivery during certain procedures. These particular applications are intended to be exemplary; the cannulae can also be used to facilitate other types of heart procedures, non-heart related procedures, and/or patient support.

Figure 1:
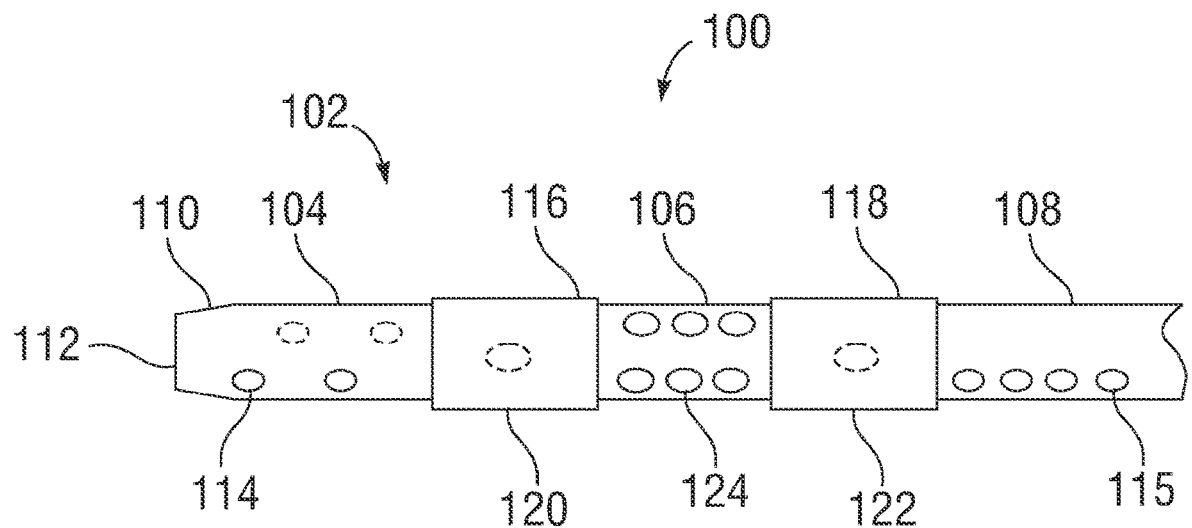
FIG. 1 shows a distal end portion of an exemplary multi-lumen cannula.

FIG. 1 shows a multi-lumen cannula embodiment 100, particularly a distal end portion 102 of the multi-lumen cannula, which comprises elongated body or shaft having a distal region 104, an intermediate region 106, and a proximal region 108. The distal end portion 102 of the multi-lumen cannula 100 is understood herein to be the end of the multi-lumen cannula inserted into the patient during a procedure. In some embodiments, the distal end portion can be inserted into a patient's vena cava. In some embodiments, the distal end portion can be positioned within a patient's vena cava so that the distal region of the distal end portion is positioned within the IVC and the proximal region of the distal end portion is positioned with the SVC, such as when the multi-lumen cannula is introduced into the patient through the patient's internal jugular vein. In other embodiments, the distal end portion can be positioned within a patient's vena cava so that the distal region of the distal end portion is positioned within the SVC and the proximal region of the distal end portion is positioned within the IVC, such as when the multi-lumen cannula is introduced into the patient through the patient's femoral vein.

Blood can be conducted from a patient's vein to an external reservoir through the multi-lumen cannula. The blood can be conducted using passive or active conduction. Passive conduction is understood herein to mean conducting blood through at least one lumen of a multi-lumen cannula without applying an external vacuum to facilitate flow. Active conduction is understood herein to mean conducting blood through at least one lumen of a multi-lumen cannula by applying an external vacuum.

Figure 2:
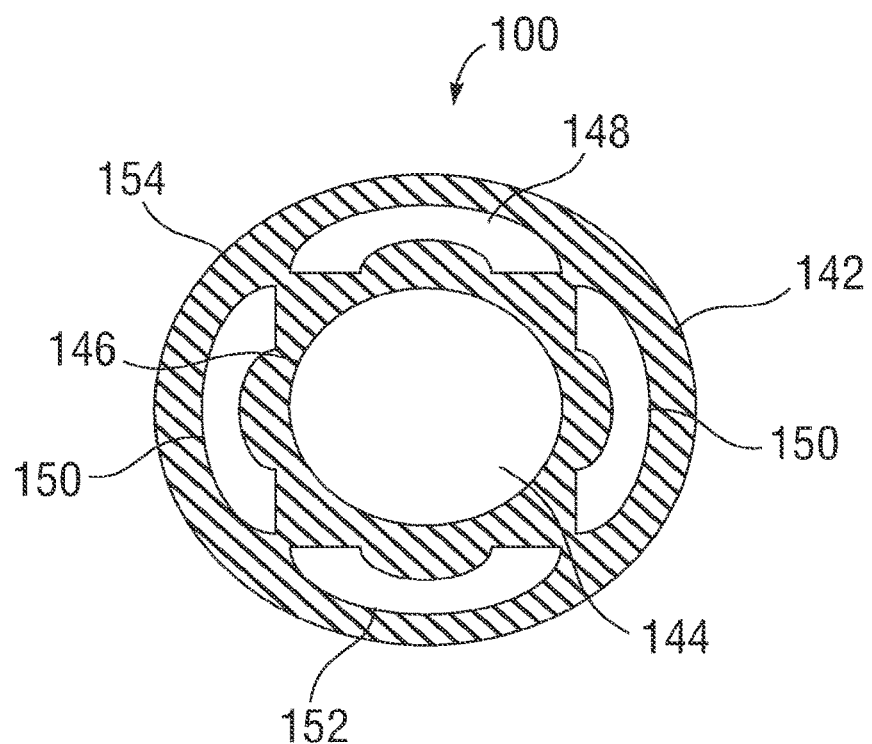
FIG. 2 is cross-sectional view of an exemplary cannula body, according to one embodiment, illustrating a central lumen and four separate sidewall lumens.

As shown in FIG. 1, the distal region 104 of the distal end portion 102 can comprise a tapered tip no that tapers to form distal end 112, which can comprise one or more distal openings (not illustrated) that can be coupled to a central lumen 144, which is illustrated in FIG. 2. Any number of distal openings suitable for facilitating fluid flow from the patient's vasculature into the central lumen 144 can be included in the distal end 112, and the distal openings can have any shape and configuration.

The distal region 104 can also comprise at least one distal fluid port 114 (which can also be referred to as a side port) (FIG. 1), which can be fluidly coupled to the central lumen 144 (FIG. 2), one or more sidewall lumens 152 (as illustrated in FIG. 2), or both the central lumen and the one or more sidewall lumens. Any number of distal fluid ports 114 can be included within the distal region 104 to conduct blood from the patient. For example, FIG. 1 illustrates a cannula embodiment wherein one or more distal fluid ports 114, such as the two distal fluid ports shown in solid lines in FIG. 1, can oppose one or more different distal fluid ports 114, such as the two distal fluid ports shown in dashed lines in FIG. 1. Including multiple distal fluid ports oriented around the perimeter of the distal region 104 can facilitate fluid conduction through the multi-lumen cannula. For example, the inclusion of a plurality of distal fluid ports 114 around the distal region 104 increases the surface area through which fluid can enter the cannula 100.

The distal fluid ports 114 can be formed by punching and/or drilling holes in the exterior perimeter of the distal region 104 through to the central lumen 144 (FIG. 2) of the multi-lumen cannula, through to one or more sidewall lumens (e.g., 152), and/or through to one or more sidewall lumens and further from the sidewall lumens through to the central lumen. In some embodiments, the distal region 104 can comprise a single lumen tube. In such embodiments, the distal fluid ports 114 can be fluidly coupled with a single central lumen, which is the only lumen in the distal region. Thus the distal fluid ports 114 can be located at any position around the single lumen tube.

As illustrated in FIG. 1, the proximal region 108 of the distal end portion 102 can also comprise a plurality of fluid ports, such as proximal fluid side ports 115. Similar to the distal fluid ports 114, proximal fluid side ports 115 can be fluidly coupled to the central lumen 144 (FIG. 2), one or more sidewall lumens, or combinations thereof. The sidewall lumens to which the proximal fluid ports may be coupled may be the same as or different from the sidewall lumens to which the distal fluid ports are coupled. In some embodiments, the one or more sidewall lumens to which the proximal fluid ports and/or the distal fluid ports are fluidly coupled can be the conduction sidewall lumens 152 illustrated in FIG. 2. The proximal fluid ports 115 can be made using the same technique described for the distal fluid ports. The number and arrangement of proximal fluid ports can be the same as or different from the number of distal fluid ports. In embodiments where the proximal fluid ports 115 are coupled to the sidewall lumen 152, the ports 115 can be arranged in an axially aligned pattern (as shown in FIG. 1) that overlies the lumen 152.

The distal fluid ports 114, proximal fluid ports 115, or combinations thereof can be configured to access blood flowing within the patient's SVC and/or IVC and conduct the blood to an external reservoir.

The distal fluid ports 114 and proximal fluid ports 115 can be configured to have any shape and any arrangement within the distal end portion 102 that is suitable for conducting blood from a biological lumen to a central lumen and/or one or more sidewall lumens. In some embodiments, the size, shape, and arrangement of the distal fluid ports and the proximal fluid ports can be selected to provide (or improve) a maximum flow requirement for a particular procedure.

Multi-lumen cannulae embodiments disclosed herein also can comprise one or more intermediate fluid ports positioned within an intermediate region of the distal end portion of the cannula. Such intermediate fluid ports can be used for a variety of purposes. In some embodiments, the intermediate fluid ports can be used to deliver a cardioplegia solution to a patient during an operation. The intermediate fluid ports also can be utilized to conduct fluids other than a cardioplegia solution (such as oxygenated blood, deoxygenated blood, etc.) to and from the patient.

An exemplary embodiment of a multi-lumen cannula comprising intermediate fluid ports is illustrated in FIG. 1. The distal end portion 102 of multi-lumen cannula 100 can comprise intermediate fluid side ports 124 positioned in the intermediate region 106 that can facilitate flow into, or out of, one or more sidewall lumens located in the sidewall of the multi-lumen cannula. In the particular embodiment illustrated in FIG. 1, a plurality of intermediate fluid ports 124 are arranged in two rows on one side of the intermediate region. Such an arrangement can be used to facilitate increased fluid flow to or from a particular target location of the patient, such as the patient's right atrium.

As with the distal and proximal fluid ports 114, 115, any size, shape, number, and/or arrangement of the intermediate fluid ports 124 can be included. The size, shape, number, and/or arrangement of the intermediate fluid ports can be selected independent of the size, shape, number, and/or arrangement of the distal and/or proximal fluid ports.

One or more of the intermediate fluid ports 124 can be independently fluidly coupled to one of the two conduction sidewall lumens 150 illustrated in FIG. 2, and the remaining intermediate fluid ports 124 can be independently fluidly coupled to the other conduction sidewall lumen 150.

The multi-lumen cannulae embodiments disclosed herein can also comprise one or more balloons capable of being inflated and deflated. In some embodiments, the balloons can be inflated to facilitate a particular medical procedure. For example, the balloons can be inflated to isolate the right atrium of the heart from the IVC and the SVC. As illustrated in FIG. 1, balloons 116 and 118 can be positioned on the exterior surface of multi-lumen cannula 100 within the distal end portion 102 of the multi-lumen cannula. Balloon 116 can be positioned between the distal region 104 and intermediate region 106, and balloon 118 can be positioned between the intermediate region and the proximal region 108.

Figure 7:
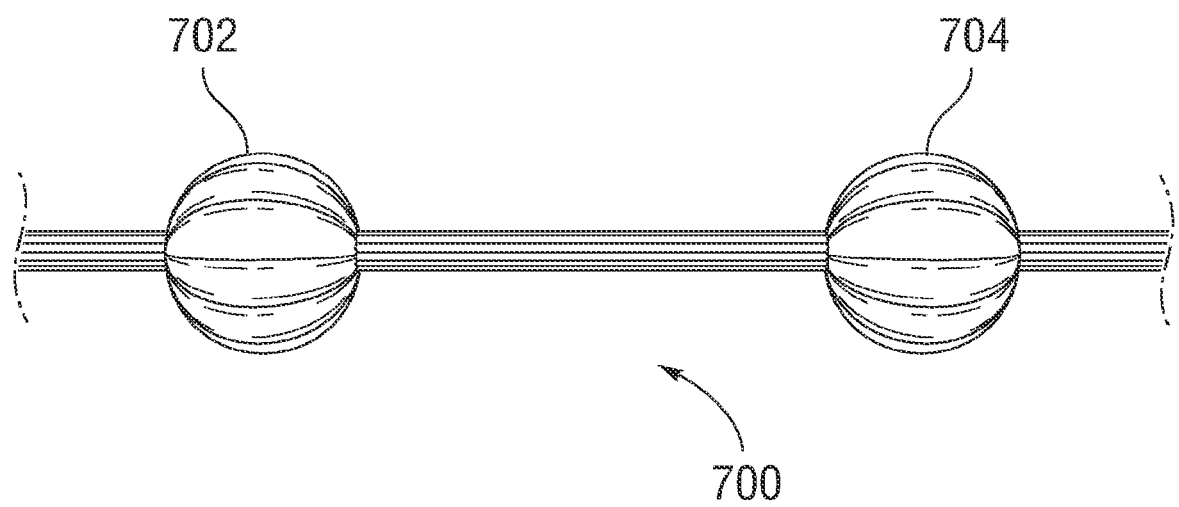
FIG. 7 shows a cannula body comprising two inflated balloons.

FIG. 1 further illustrates balloon ports 120 and 122, which can be positioned underneath balloons 116 and 118, respectively. The balloon ports 120 and 122 can pass through the exterior perimeter of the multi-lumen cannula 100 to at least one sidewall lumen that runs parallel to the central lumen 144 (FIG. 2), such as balloon sidewall lumen 148 (FIG. 2). Balloon ports 120 and 122 can be used to conduct an inflation fluid (e.g., air, a saline solution, or other liquid) to and from balloons 116 and 118 to inflate and deflate the balloons during a procedure. FIG. 7 illustrates an embodiment of a multi-lumen cannula 700 comprising two inflated balloons 702 and 704.

In some embodiments, a single sidewall lumen 148 can be included to conduct an inflation fluid to and from both balloon ports 120 and 122. Balloons 116 and 118 can therefore be inflated and deflated at substantially the same time by conducting the inflation fluid through the single balloon sidewall lumen 148 to both balloon ports 120 and 122. In other embodiments, each balloon can be coupled to an independent lumen such that each balloon can be inflated or deflated at different times.

FIG. 2 is a cross-sectional view of the multi-lumen cannula 100 taken proximal to the proximal fluid ports 115. FIG. 2 illustrates a circumferential arrangement of the plurality of sidewall lumens (e.g., conduction sidewall lumens 150 and 152 and balloon sidewall lumen 148) with respect to the central lumen 144. Referring to FIG. 2, the multi-lumen cannula 100 comprises an outer perimeter 142 and an inner perimeter 146 surrounding the central lumen 144. The outer perimeter 142 and an inner perimeter 146 define a sidewall 154 of the cannula 100 therebetween with the lumens 148, 150, 152 being formed in the sidewall 154.

Figure 3:
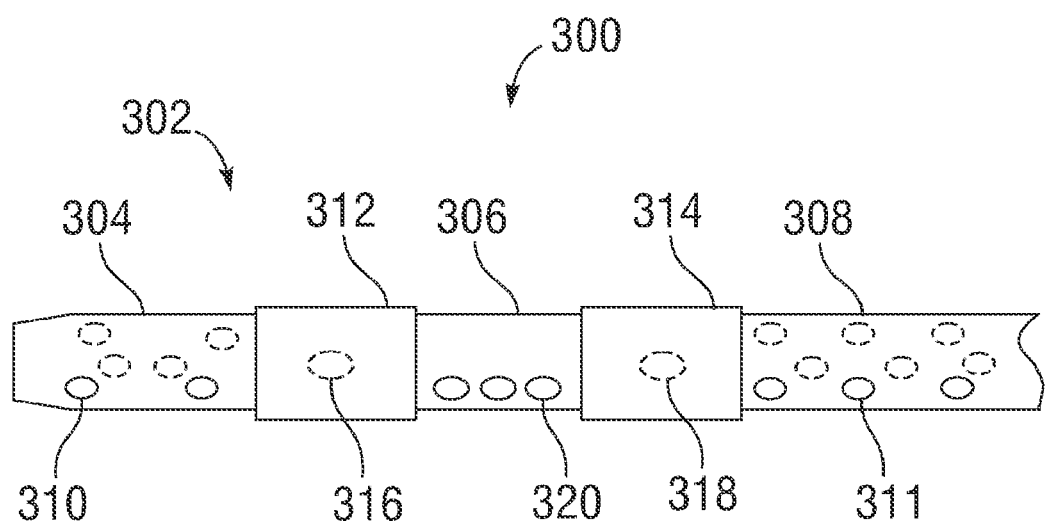
FIG. 3 shows a distal end portion of another exemplary multi-lumen cannula.
Figure 4:
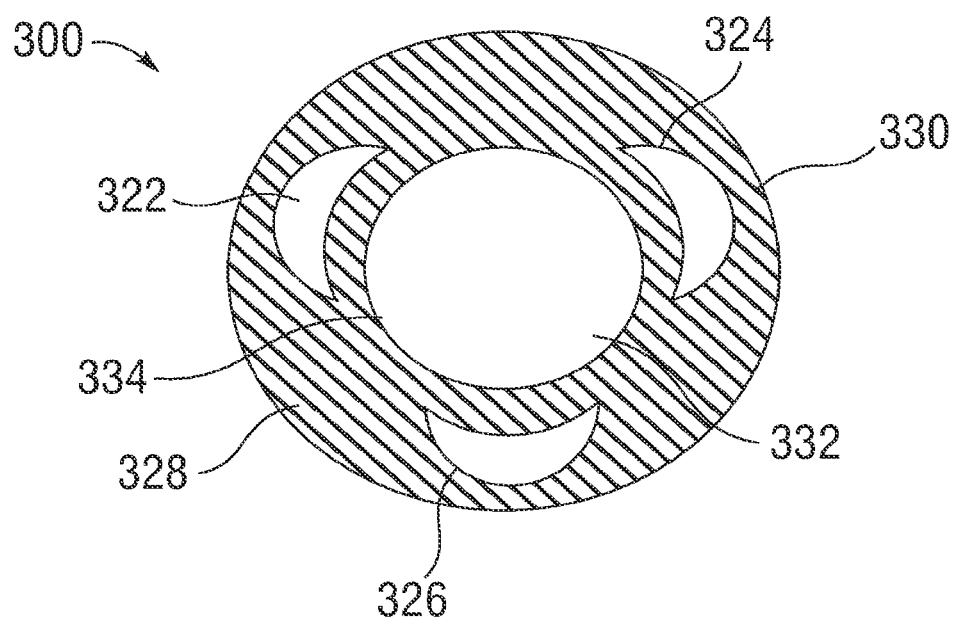
FIG. 4 is a cross-sectional view of an exemplary cannula body, according to one embodiment, illustrating a central lumen and three separate sidewall lumens.
Figure 5:
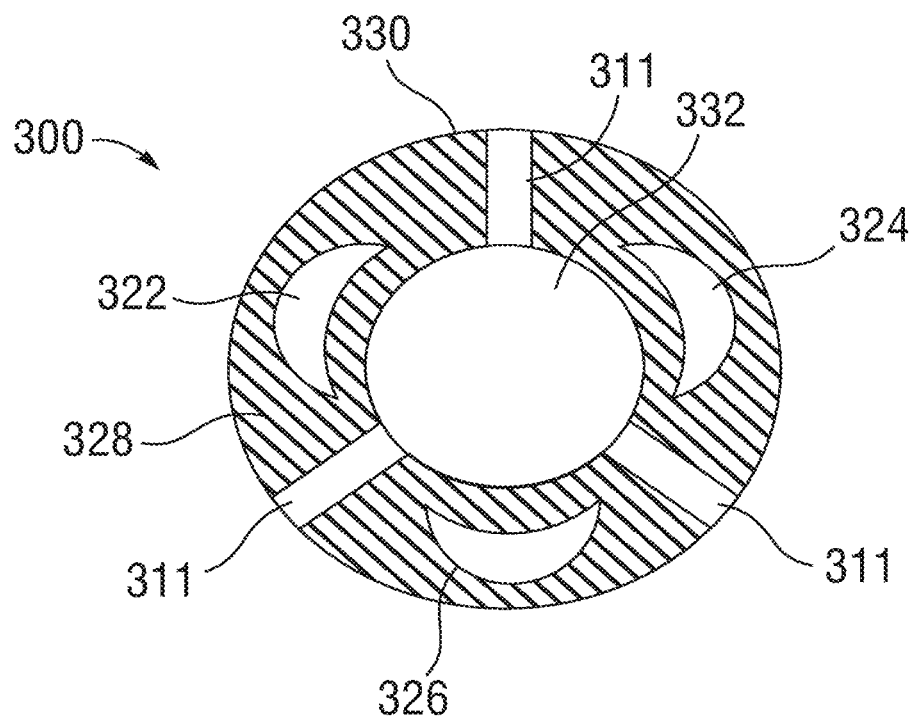
FIG. 5 is a cross-sectional view of an exemplary cannula body, according to one embodiment, illustrating a central lumen fluidly coupled to ports formed within the cannula.

Another embodiment of the disclosed multi-lumen cannulae is illustrated in FIGS. 3-5. As illustrated in FIG. 3, a distal end portion 302 of multi-lumen cannula 300 comprises a distal region 304, an intermediate region 306, and a proximal region 308. The distal region 304 can comprise a plurality of distal fluid ports 310, and the proximal region 308 of the distal end portion can comprise a plurality of proximal fluid ports 311. The proximal fluid ports 311 can be fluidly coupled to a common central lumen 332, as shown in FIG. 5. Similarly, the distal fluid ports 310 can also be fluidly coupled to the central lumen 332.

FIG. 4 is a cross-section taken at a point proximal to the proximal region 308. As illustrated in FIG. 4, a plurality of different sidewall lumens 322, 324, and 326 can be circumferentially positioned within sidewall 328 between the outer perimeter 330 and inner perimeter 334. The sidewall lumens 322, 324, and 326 can run parallel to a central lumen 332.

FIG. 5 is another cross-sectional view of the multi-lumen cannula 300 taken within the proximal region 308 of the distal end portion 302. FIG. 5 illustrates how proximal fluid ports 311 are fluidly coupled to central lumen 332. The proximal fluid ports 311, as illustrated in FIG. 5, do not pass through sidewall lumens 322, 324, or 326, thereby segregating flow through the proximal fluid ports to the central lumen 332 from flow through sidewall lumens 322, 324, and 326. The proximal fluid ports 311 can be arranged as illustrated in FIG. 5 so that each proximal fluid port is positioned between sidewall lumens 322, 324, and 326. As sidewall lumens 322, 324, and 326 can terminate prior to entering the distal region 304, the distal fluid ports 310 can be arranged in any orientation independent of proximal fluid ports 311. In some embodiments, however, the distal fluid ports can be arranged the same as the proximal fluid ports.

As illustrated in FIG. 3, intermediate portion 306 comprises a plurality of intermediate fluid ports 320. The intermediate fluid ports 320 are fluidly coupled to sidewall lumen 326 and thus may be placed along one side of the intermediate region 306 adjacent to the sidewall lumen 326. The intermediate fluid ports 320 are aligned in one row on one side of the multi-lumen cannula in this particular embodiment; however, this illustration is exemplary and in other embodiments, the intermediate fluid ports 320 can be differently arranged. As discussed above, including the intermediate ports 306 on one side of the multi-lumen cannula can facilitate procedures wherein the right atrium of the patient is to be isolated from blood flowing through a patient's vena cava. The intermediate fluid ports 306 can be positioned to face the entrance to the right atrium and facilitate fluid delivery specifically to the right atrium.

Multi-lumen cannula 300, as illustrated in FIG. 3, can further comprise two balloons 312 and 314 connected to the exterior of the distal end portion 302. Balloon 312 covers balloon port 316 and balloon 314 covers balloon port 318. Each balloon port 316 and 318 can be independently fluidly coupled to a different sidewall lumen. For example, balloon port 316 can be fluidly coupled to sidewall lumen 322, which is illustrated in FIGS. 4 and 5, and balloon port 318 can be fluidly coupled to sidewall lumen 324, which is also illustrated in FIGS. 4 and 5. Using this configuration, each balloon 312 and 314 can be connected to a separate sidewall lumen thereby permitting selective inflation and/or deflation of the balloons.

In some embodiments, the balloons can be inflated (and ultimately deflated) sequentially to ensure that the balloon positioned within the IVC is positioned in a suitable location before the balloon positioned within the SVC is inflated. For example, the balloon that is to be positioned within the IVC can be positioned so that it blocks the right atrium from blood flowing from the IVC to the right atrium. In some embodiments, the balloon is positioned within the IVC so that the outer periphery of the balloon sits approximately 4 cm from the inferior end of the right atrium to avoid covering the patient's hepatic veins and thereby prevent disrupted blood flow to the hepatic system. Alternatively, the SVC balloon can be inflated before the IVC balloon.

In other procedures, the balloons 316, 318 can be inflated (and ultimately deflated) simultaneously, or substantially simultaneously. Simultaneous inflation can be accomplished by administering an inflation fluid into the two independent sidewall lumens 322, 330 at the same time, such as from a common source.

Figure 6:
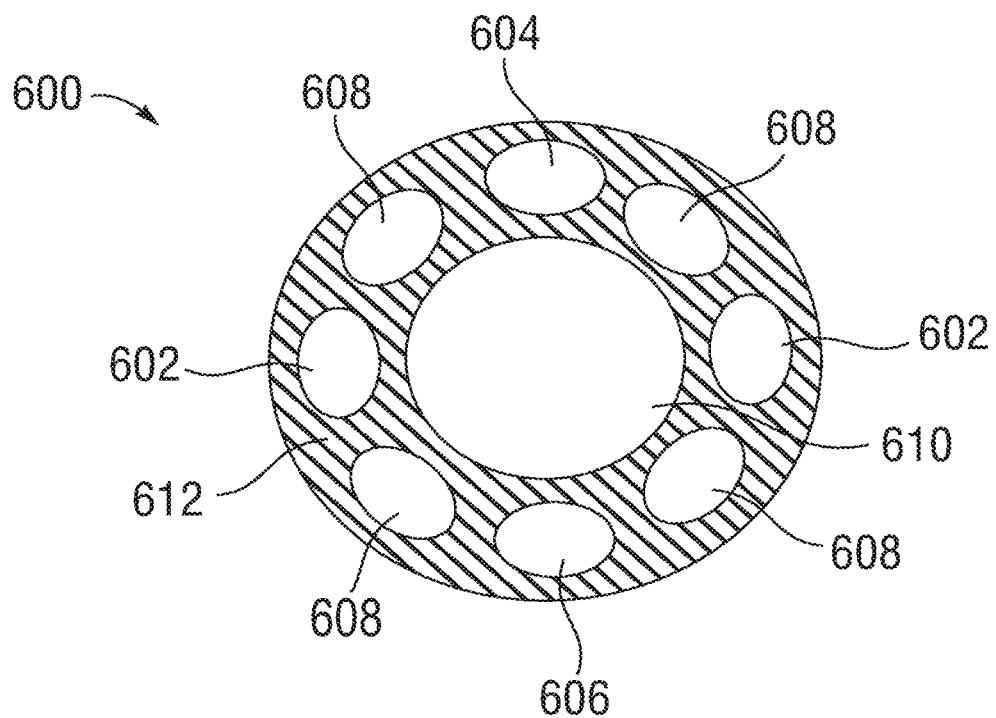
FIG. 6 is a cross-sectional view of an exemplary cannula body comprising nine different sidewall lumens spaced around a central lumen.

FIG. 6 is a cross-sectional view of another exemplary multi-lumen cannula 600. Cannula 600 comprises a plurality of sidewall lumens arranged circumferentially around a central lumen 610. The plurality of sidewall lumens can comprise, for example, two independent sidewall lumens 602 coupled to intermediate ports located in an intermediate region between two balloons, two independent sidewall lumens 604 and 606 independently coupled to the two balloons, and four sidewall lumens 608 coupled to distal fluid ports, proximal fluid ports, or any combination thereof. The sidewall lumens can be positioned substantially equidistant from one another, or they can be positioned with an uneven spacing. Any suitable arrangement can be chosen. Additionally, each sidewall lumen can vary in size with respect to the other sidewall lumens, and any number of sidewall lumens can be included.

The cannula can also comprise a proximal end portion connected to, or continuing from the distal end portion. The proximal end portion of the multi-lumen cannula can comprise a handle portion suitable for manipulating/controlling flow through the multi-lumen cannula. In some embodiments, the handle can be used to deliver a fluid to the patient. For example, the cardioplegia solution and/or the inflation fluid discussed above can be delivered to the different intermediate fluid ports and/or balloon ports disclosed herein via the corresponding conduction sidewall lumens and/or balloon sidewall lumens that extend from the proximal end portion of the elongated body to the distal end portion of the elongated body. In some embodiments, the handle can be used to facilitate oxygenated blood flow into the cannula from an external heart/lung machine or other source during ECMO.

Figure 8:
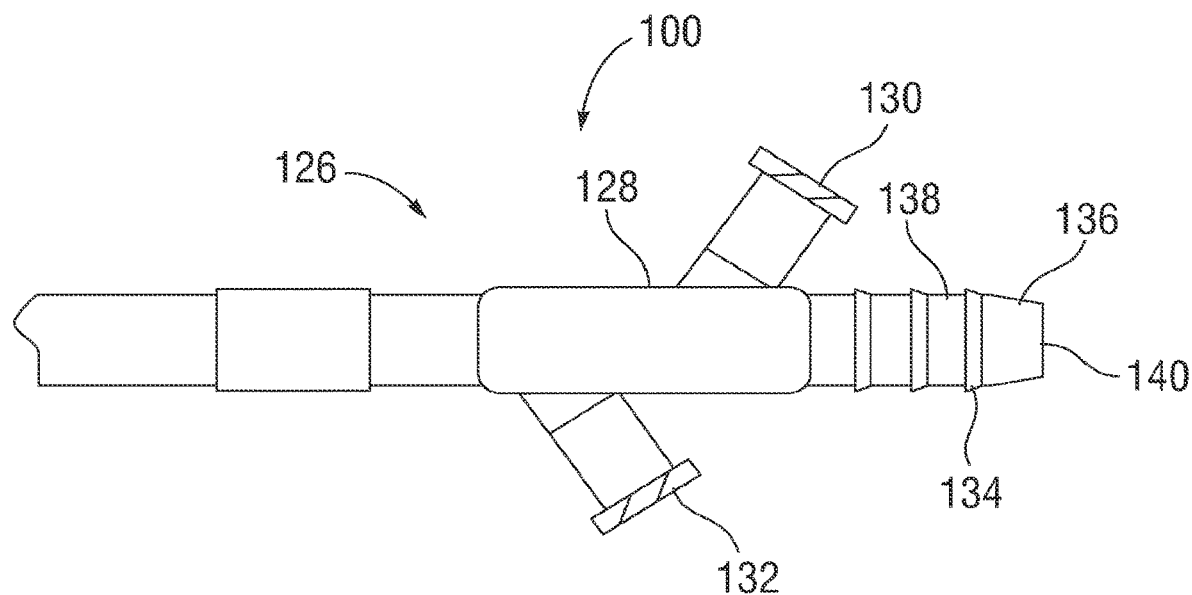
FIG. 8 shows a proximal end portion of the multi-lumen cannula of FIG. 1.
Figure 9:
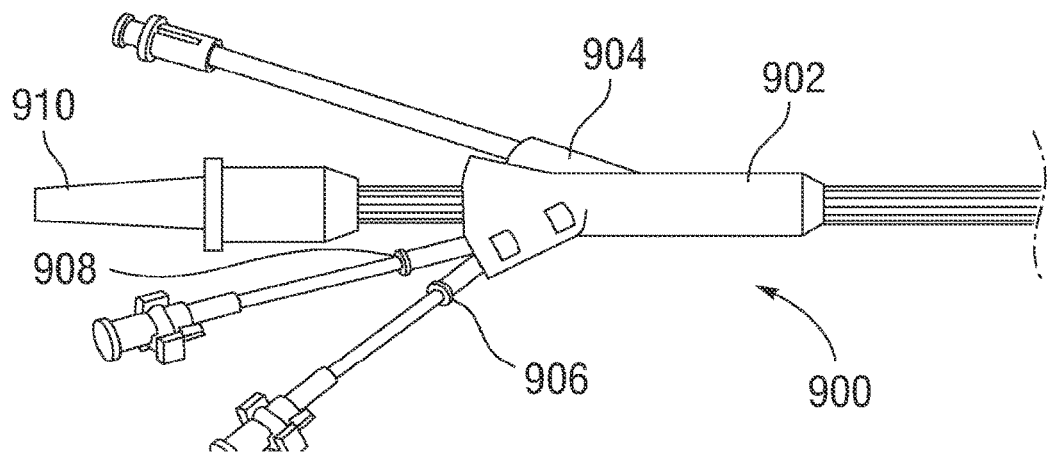
FIG. 9 shows an exemplary cannula handle that includes various tubes connected to respective lumens of the multi-lumen cannula.

Exemplary embodiments of a handle that can be included with a multi-lumen cannula are illustrated in FIGS. 8 and 9. As illustrated in FIG. 8, the handle 128 can be positioned at the proximal end portion 126 of multi-lumen cannula 100 and can comprise two external delivery ports 130 and 132 that extend outward from handle 128. These external delivery ports 130 and 132 can be connected to one or more delivery devices (not illustrated), such as a delivery device or fluid source that provides a cardioplegia solution, an inflation fluid, and/or blood to the patient using multi-lumen cannula boo. The two external delivery ports 130 and 132 can be arranged in any suitable configuration. Additionally, any number of external delivery ports 130 and/or 132 can be attached to the handle.

One or more adaptor ridges 134 and tapered tip 136 can be included in the proximal region 138 of the proximal end portion 126, as illustrated in FIG. 8. Tapered tip 136 and adaptor ridges 134 can facilitate connection to a vacuum device, which can actively conduct fluid from the cannula through one or more openings located in proximal end 140. In some embodiments, the proximal region 138 of the proximal end portion 126 can comprise a single lumen tube.

Another embodiment of a multi-lumen cannula comprising a handle is illustrated in FIG. 9. Cannula 900 comprises a handle 902 including three delivery ports 904, 906, and 908, and a proximal region 910.

The sidewall lumens of the multi-lumen cannula can terminate at different axial locations along the cannula, independently of the central lumen. For example, a sidewall lumen that is fluidly coupled to an intermediate fluid port within an intermediate region of the distal end portion can terminate within the intermediate region so that it does not extend into a distal region. In some embodiments, the distal region of the distal end portion can comprise a single lumen tube. Sidewall lumens fluidly coupled to balloon ports also can also be configured to terminate prior to the distal region of the distal end portion of the cannula. Thus, the number of lumens can decrease moving axially toward the distal end of the cannula.

The multi-lumen cannulae disclosed herein can comprise a variety of suitable materials, including polymers (e.g., polyurethane, nylon, polytetrafluoroethylene, polyvinylchloride, and the like), metals (e.g., stainless steel or Ninitol), alloys, composites, or combinations thereof. In certain embodiments, the cannula can be extruded or wire wound. Extruded embodiments can be sufficiently strong such that exterior support (such as a metal coil) around the cannula may not be necessary. In some embodiments, however, the cannula can be reinforced with a material that promotes crush resistance, such as a coil or sheath.

The diameter of the elongated body of a multi-lumen cannula can vary thereby affording different cannula embodiments that can be used in differently sized patients and in different biological lumens present in a patient's vasculature, such as the vena cava (including the SVC and the IVC), the internal jugular vein, the femoral vein, and the like. For example, the elongated body of a multi-lumen cannula can have an outer diameter of about 0.2 inches to about 0.4 inches, with some embodiments having an outer diameter of about 0.27 inches to about 0.33 inches. The diameter of the cannula can be larger in the regions of the elongated body that include a handle or a balloon.

As the multi-lumen cannulae disclosed herein can be introduced into the patient through the femoral vein or the internal jugular vein or other vessels, the length of a particular cannula can be selected to accommodate the particular biological lumen into which it is to be placed.

In some embodiments, the elongated body can have a length of about 55 cm to about 65 cm from the distal tip to the end of the proximal region of the distal end portion. Such embodiments can be used for a femoral approach. In other embodiments, the elongated body can have a length of about 20 cm to about 45 cm from the distal tip to the end of the proximal region of the distal end portion. Such embodiments can be used for an internal jugular approach.

Figure 10:
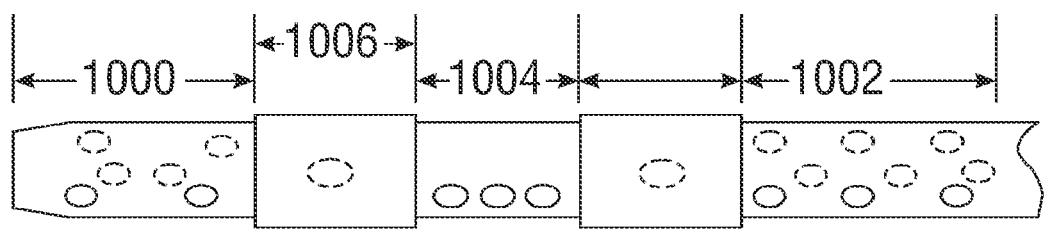
FIG. 10 shows the dimensions of particular portions of the distal end region of an exemplary multi-lumen cannula.

Each of the distal region and the proximal region of the distal end portion of the elongated body can have a length ranging from about 3 cm to about 20 cm. Referring to FIG. 10 as an example, the distal region can have a length woo ranging from about 3 cm to about 20 cm as measured from the distal end of the cannula to the distal end of the balloon positioned closest to the distal end of the cannula. The proximal region can have a length 1002 ranging from about 3 cm to about 20 cm as measured from the proximal end of a proximal fluid port that is positioned closest to the proximal end of the cannula to the proximal end of the balloon positioned closest to the proximal end of the cannula.

In embodiments wherein a femoral approach is used, the distal region of the distal end portion of the elongated body can have a length 1000 ranging from about 3 cm to about 7 cm and the proximal region of the distal end portion can have a length 1002 ranging from about 5 cm to about 20 cm. When a multi-lumen cannula is inserted through an internal jugular vein of the patient, the distal region of the distal end portion can have a length woo of about 5 cm to about 20 cm, and the proximal region of the distal end portion can have a length 1002 of about 3 cm to about 10 cm.

The balloons used with the disclosed multi-lumen cannulae can be made of any suitable material, such as, but not limited to, latex, silicone, polyethylene, polyurethane, or combinations thereof. The outer surface of the balloons can be textured or smooth. The balloons can be bonded to the exterior surface of the cannulae using a suitable adhesive typically used in the art. The balloons can be separated by a distance 1004 of about 5 cm to about 15 cm, as measured from the proximal end of the balloon positioned closest to the distal end to the distal end of the balloon positioned closest to the proximal end. In some embodiments, the distance 1004 is about 14 cm. The balloons can have a length 1006 of up to about 2 cm, with some embodiments comprising balloons having a length 1006 of about 1 cm.

Sidewall lumens can be formed within a multi-lumen cannula by using a suitable extrusion method, for example. In particular disclosed embodiments, the cross-sectional area of the sidewall lumens can be maximized to facilitate actively conducting blood and/or a fluid to and from the patient. The cross-sectional area of the sidewall lumens also can be configured to minimize the amount of cannula material present within the body of the multi-lumen cannula so as to maximize the area of each sidewall lumen and/or the central lumen.

Additionally, the distance or area between the sidewall lumens and the outer perimeter of the cannula and/or the outer perimeter of the central lumen can be minimized to facilitate use. In some embodiments, a suitable distance or area between the sidewall lumens and the outer perimeter of the cannula and/or the outer perimeter of the central lumen is maintained to prevent, or substantially prevent kinking of the cannula.

Figure 11:
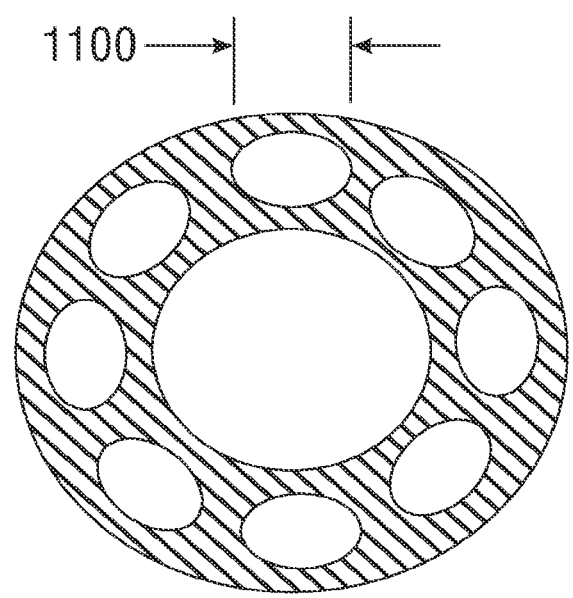
FIG. 11 shows a certain dimension of an exemplary sidewall lumen.
Figure 12:
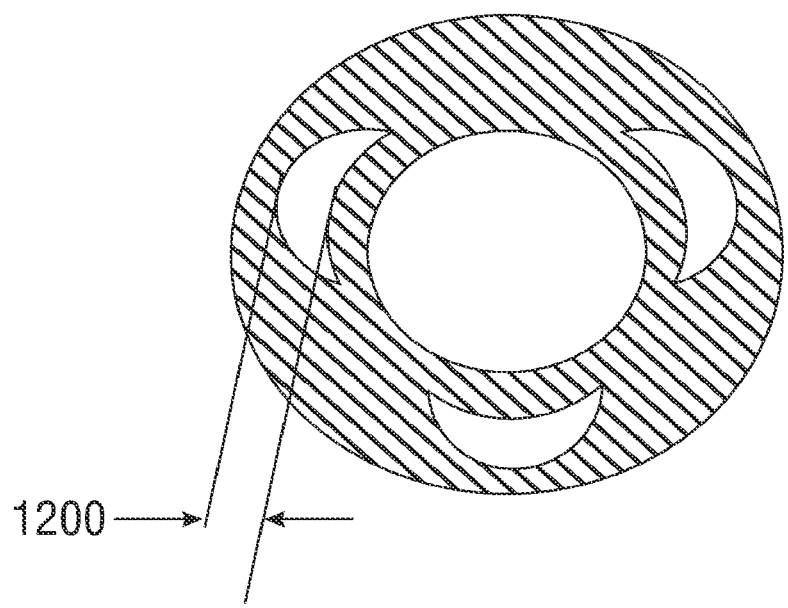
FIG. 12 shows a certain dimension of another exemplary sidewall lumen.

In different embodiments, any suitable spacing/positioning can be used. The sidewall lumens also may have any shape and/or size suitable for performing a desired function, such as cardioplegia delivery, active or passive conduction, inflation and/or deflation. In some embodiments, the sidewall lumens can be oval-shaped and have a major diameter 1100, as illustrated in FIG. 11, of about 0.02 inches to about 0.04 inches, with some embodiments having a major diameter 1100 of about 0.028 inches. In other embodiments, the sidewall lumens can be crescent shaped having a width 1200, as illustrated in FIG. 12, ranging from about 0.01 inches to about 0.020 inches, such as about 0.015 inches. The sidewall lumens can be positioned to be about 0.01 inches from the outer perimeter of the cannula body and about 0.01 inches from the outer perimeter of the central lumen. The central lumen can have a diameter of about 0.15 inches to about 0.3 inches. In exemplary embodiments, the diameter of the central lumen can be about 0.2 inches to about 0.24 inches.

Figure 13:
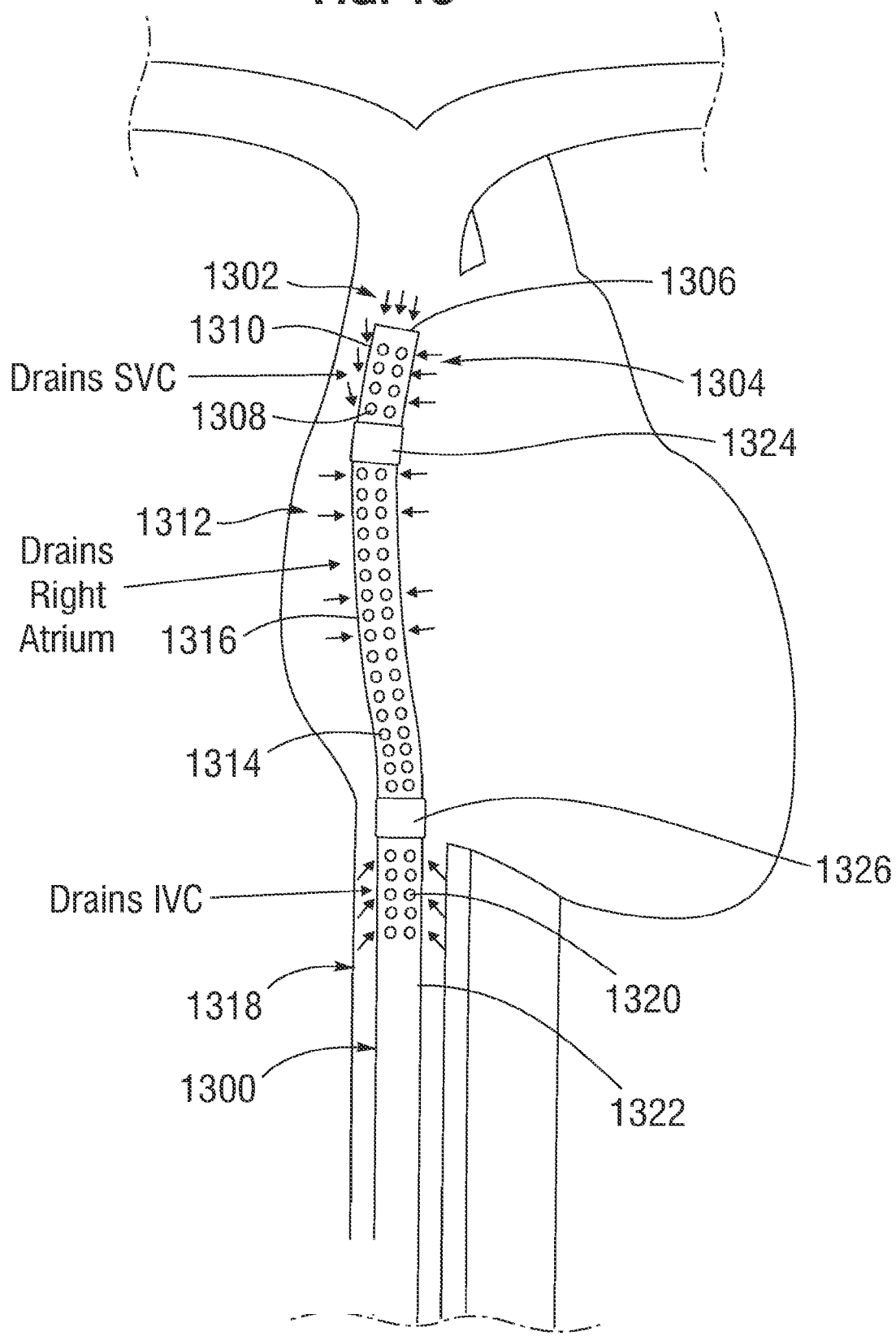
FIG. 13 shows an exemplary use of a multi-lumen cannula wherein the balloons are not inflated and all of the ports and lumens are used for common blood drainage.

The disclosed multi-lumen cannulae can be used in various different procedures. In some implementations, all or some of the lumens and ports can be used for common blood drainage from the vena cava and right atrium without inflating the balloons to isolate the right atrium. FIG. 13 illustrates one such example. In such implementations, lumens of the cannula (such as the central lumen and one or more sidewall lumens) can be used to drain blood from all ports to a common external reservoir. As illustrated in FIG. 13, the multi-lumen cannula 1300 is positioned within a patient's vena cava and blood flowing from the SVC (represented by arrows 1302 and 1304) flows into a central lumen through distal end 1306 and also through distal fluid ports 1308 in the distal region 1310. Blood drained from the right atrium 1312 flows into the cannula through intermediate ports 1314 in intermediate region 1316, such as into one or more of the sidewall lumens. Blood flowing from the IVC 1318 can flow into the cannula through proximal fluid ports 1320 of proximal region 1322, such as into the central lumen or into one or more of the sidewall lumens. In the embodiment illustrated in FIG. 13, balloons 1324 and 1326 are left deflated such that the right atrium is not isolated from the SVC and IVC. Thus, all of the ports and lumens are used for the same purpose to drain blood from the vena cave and right atrium region. This implementation of the multi-lumen cannula can be useful during aortic valve repair, mitral valve repair, or other cardiac procedures that do not require incision into the right portion of the heart.

Figure 14:
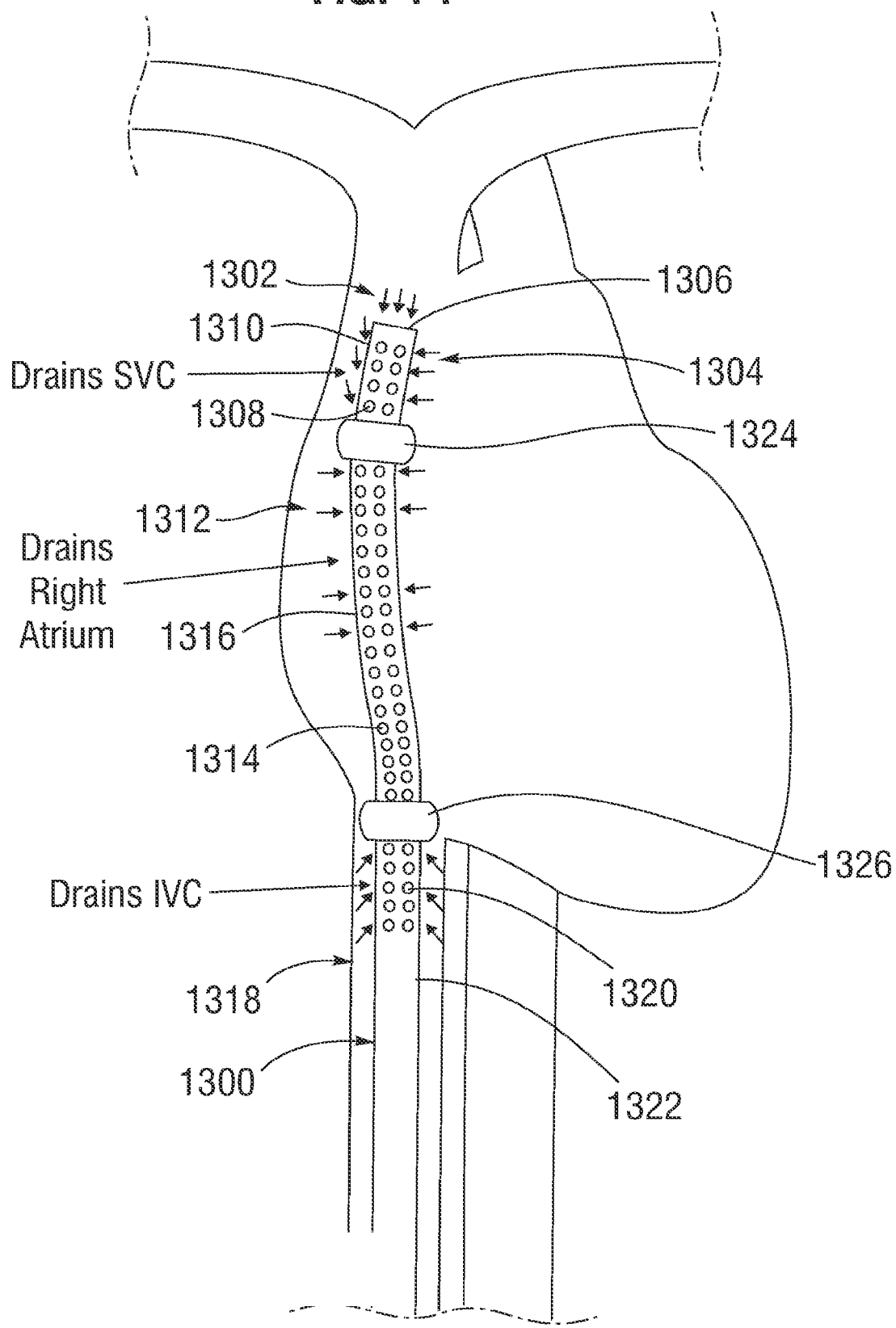
FIG. 14 shows an exemplary use of a multi-lumen cannula wherein the balloons are inflated, the ports in the distal region and proximal region of the cannula are used to drain blood from the SVC and the IVC, and ports in the intermediate region are used to drain blood from the right atrium independent of the SVC and IVC.

Another exemplary implementation of the multi-lumen cannula 1300 is illustrated in FIG. 14. In this embodiment, balloons 1324 and 1326 are inflated to isolate the right atrium from the SVC and the IVC, and the blood drained from the right atrium can be isolated from the blood drained from the SVC and the IVC. For example, blood drained from the SVC (represented by arrows 1302 and 1304) and blood drained from the IVC (represented by arrows 1318) can be conducted from the patient through a central lumen to a first location, while blood flowing from the patient's right atrium (represented by arrows 1312) can be conducted through one or more sidewall lumens to a second location to segregate the blood.

In other implementations, the disclosed multi-lumen cannulae can be used for cardioplegia delivery during a heart procedure. In such implementations, the two balloons are inflated to isolate the right atrium from the SVC and the IVC. The central lumen and/or one or more of the sidewall lumens is used to drain blood from the SVC and the IVC, such as to an external cardiotomy reservoir for recirculation, while intermediate fluid ports of the cannula are fluidly coupled to one or more sidewall lumens and selectively drain blood from the right atrium to an external cell saver for hemoconcentration. This selective drainage can occur when a cardioplegia solution is being delivered to allow the cardioplegia solution to be selectively removed from circulation. This use of the intermediate ports and sidewall lumens can reduce the need for hemoconcentration at a later stage in the operation thereby reducing any negative impacts on the patient's blood chemistry. Single- or multiple-dose cardioplegia can be delivered with the disclosed multi-lumen cannulae.

Figure 15:
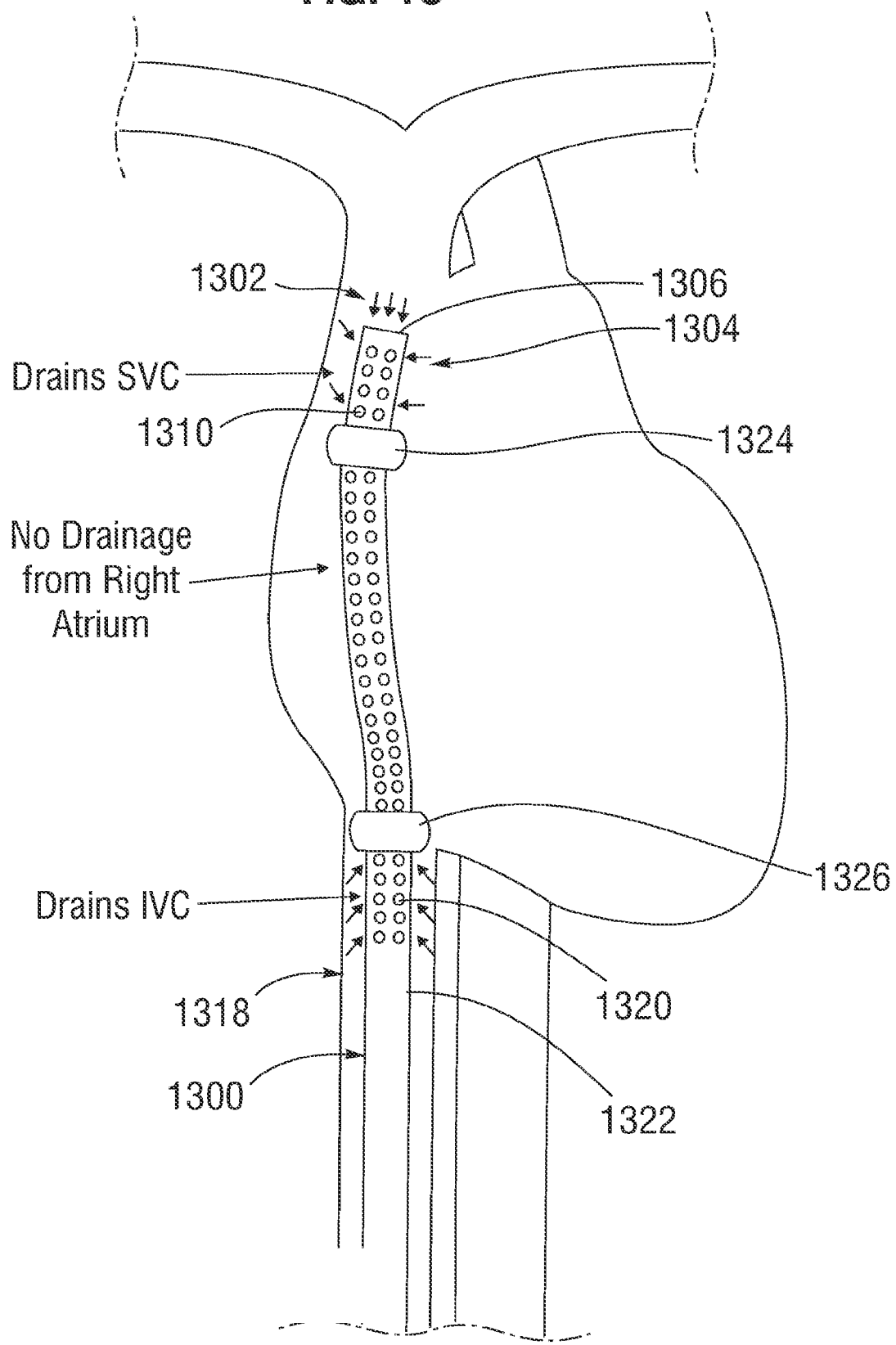
FIG. 15 shows an exemplary use of a multi-lumen cannula wherein the balloons are inflated, ports in the distal region and proximal region of the cannula are used to drain blood from the SVC and the IVC, and no flow occurs through ports in the intermediate region to or from the right atrium.

The disclosed multi-lumen cannulae also can be used during a procedure that requires incision into the right portion of the heart, such as the right atrium (e.g., tricuspid valve repair). In such embodiments, the multi-lumen cannulae can be manipulated to facilitate the procedure by stopping flow through the sidewall lumens in communication with the ports in the intermediate region between the two balloons such that no fluid is conducted into or out of the right atrium. Blood can then be drained from the SVC and the IVC through the central lumen and/or sidewall lumens without effecting the right atrium. The surgeon may then optionally snare around the right atrium prior to performing the desired right-heart procedure. FIG. 15 illustrates an exemplary implementation of the multi-lumen cannula 1300 for blood drainage during a right-heart surgical procedure, such as a tricuspid valve repair. Balloons 1324 and 1326 are inflated to isolate the patient's right atrium from the SVC and the IVC. Blood flowing from the SVC (represented by arrows 1302) is conducted through a central lumen through distal end 1306 and distal fluid ports 1308 located in distal region 1310. Blood flowing from the IVC (represented by arrows 1318) is conducted from the patient through proximal fluid ports 1320 located in proximal region 1322 into the central lumen and/or one or more sidewall lumens.

In other implementations, the disclosed multi-lumen cannulae can be used in an ECMO procedure, such as veno-arterial ECMO. In some implementations, the central lumen and optionally one or more of the sidewall lumens can be used to facilitate blood drainage from the SVC and the IVC, while one or more of the sidewall lumens are used to re-infuse oxygenated blood into the right atrium from an external source, such as a heart/lung machine. The re-infused blood can be introduced into the right atrium through intermediate ports positioned between the two balloons of the cannula. In such embodiments, the balloons need not be inflated; however, the balloons of the multi-lumen cannulae can be inflated to avoid mixing oxygenated and deoxygenated blood, thereby improving the oxygen saturation of blood being delivered to the right atrium. FIG. 16 illustrates an exemplary implementation use multi-lumen cannula 1300 to drain deoxygenated blood from the SVC and the IVC while re-infusing oxygenated blood into the right atrium. Blood flowing from the patient's SVC (represented by arrows 1302 and 1304) is conducted through distal end 1306 and through distal fluid ports 1308 of distal region 1310. Blood flowing from the IVC (represented by arrows 1318) is conducted into the cannula through proximal fluid ports 1320. Balloons 1324 and 1326 are inflated in FIG. 16 to isolate the right atrium. Intermediate fluid ports 1314 in the intermediate region 1316 are fluidly coupled to one or more sidewall lumens and selectively deliver oxygenated blood into the right atrium.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically, chemically, electrically, magnetically, or otherwise coupled or linked and does not exclude the presence of intermediate elements between the coupled items absent specific contrary language.

In view of the many possible embodiments to which the principles of the disclosed technology may be applied, it should be recognized that the illustrated embodiments are only preferred examples of the disclosed technology and should not be taken as limiting the scope of the technology. Rather, the scope of the disclosed technology is at least as broad as the following claims. We therefore claim all that comes within the scope of these claims.

We claim:

1. A cannula comprising:
   a plurality of independent lumens;
   a first balloon and a second balloon, wherein the first balloon and the second balloon are axially spaced apart for positioning the first balloon within an inferior vena cava and positioning the second balloon within a superior vena cava, and wherein the first balloon and the second balloon are inflatable for fluidly isolating a right atrium from the inferior vena cava and the superior vena cava;
   a plurality of proximal fluid ports located proximal of the first and second balloons and fluidly coupled to a central lumen of the plurality of independent lumens for conducting a first portion of blood from the inferior vena cava;
   one or more distal fluid ports located distal of the first and second balloons and fluidly coupled to the central lumen for conducting a second portion of blood from the superior vena cava;
   one or more first intermediate fluid ports located between the first and second balloons and fluidly coupled to a first side wall lumen of the plurality of independent lumens for conducting a first fluid away from the right atrium;
   one or more second intermediate fluid ports located between the first and second balloons and fluidly coupled to a second side wall lumen of the plurality of independent lumens for conducting a second, different fluid to the right atrium; and
   a first balloon port fluidly coupling the first balloon to a third side wall lumen of the plurality of independent lumens;
   wherein each of the first, second, and third side wall lumens extends parallel to the central lumen, wherein the first, second, and third side wall lumens are arranged circumferentially around the central lumen; and
   wherein, for the fluid coupling of the plurality of proximal fluid ports to the central lumen, the proximal fluid ports extend radially through a side wall of the cannula, wherein a first one of the proximal fluid ports extends between the first and second side wall lumens, a second one of the proximal fluid ports extends between the second and third side wall lumens, and a third one of the proximal fluid ports extends between the first and third side wall lumens.

2. The cannula of claim 1, wherein the one or more distal fluid ports are located along a distal end portion of the cannula, and the central lumen extends from the distal end portion to a proximal end portion of the cannula.

3. The cannula of claim 2, wherein the first and second side wall lumens each terminate proximal of the distal end portion of the cannula.

4. The cannula of claim 3, wherein the one or more distal fluid ports comprise a plurality of distal fluid ports having a different arrangement relative to the plurality of proximal fluid ports.

5. The cannula of claim 2, wherein the one or more distal fluid ports comprise a plurality of distal fluid ports, and wherein, for the fluid coupling of the distal fluid ports to the central lumen, the distal fluid ports extend radially through the side wall of the cannula.

6. The cannula of claim 1, further comprising a second balloon port fluidly coupling the second balloon to a fourth side wall lumen of the plurality of independent lumens.

7. The cannula of claim 6, wherein the first balloon and the second balloon are each independently inflatable.

8. The cannula of claim 1, wherein each of the first, second, and third side wall lumens has a crescent-shaped cross-section.

9. The cannula of claim 1, wherein the first, second, and third side wall lumens are spaced a same distance in a radial direction from the central lumen.

10. The cannula of claim 9, wherein the first, second, and third side wall lumens are equally spaced from each other in a circumferential direction around the central lumen.

11. A cannula comprising:
    a plurality of independent lumens;
    a first balloon and a second balloon, wherein the first balloon and the second balloon are axially spaced apart for positioning the first balloon within an inferior vena cava and positioning the second balloon within a superior vena cava;
    a plurality of proximal fluid ports located proximal of the first and second balloons and fluidly coupled to a central lumen of the plurality of independent lumens;
    one or more intermediate fluid ports located between the first and second balloons and fluidly coupled to a first side wall lumen of the plurality of independent lumens;
    a first balloon port fluidly coupling the first balloon to a second side wall lumen of the plurality of independent lumens; and
    a second balloon port fluidly coupling the second balloon to a third side wall lumen of the plurality of independent lumens;
    wherein each of the first, second, and third side wall lumens extends parallel to the central lumen, wherein the first, second, and third side wall lumens are arranged circumferentially around the central lumen; and wherein, for the fluid coupling of the plurality of proximal fluid ports to the central lumen, the proximal fluid ports extend radially through a side wall of the cannula, wherein a first one of the proximal fluid ports extends between the first and second side wall lumens, a second one of the proximal fluid ports extends between the second and third side wall lumens, and a third one of the proximal fluid ports extends between the first and third side wall lumens.

12. The cannula of claim 11, wherein each of the first balloon and the second balloon is independently inflatable.

13. The cannula of claim 11, further comprising one or more distal fluid ports located in a distal portion of the cannula that is distal relative to the first and second balloons, each of the one or more distal fluid ports fluidly coupled to the central lumen.

14. The cannula of claim 13, wherein the first, second, and third side wall lumens each terminate proximal of the distal portion of the cannula, and wherein the one or more distal fluid ports comprise a plurality of distal fluid ports having a different arrangement relative to the plurality of proximal fluid ports.

15. The cannula of claim 11, wherein one or more of the first, second, or third side wall lumens has a crescent-shaped cross-section.

* * * * *